United States Patent
Tsuchita et al.

(10) Patent No.: US 7,939,099 B2
(45) Date of Patent: May 10, 2011

(54) SUSTAINED IMPROVER OF MUSCULAR FATIGUE

(75) Inventors: Hiroshi Tsuchita, Odawara (JP); Masato Saito, Odawara (JP); Toshikazu Kamiya, Chiyoda (JP); Miho Komatsu, Tsukuba (JP)

(73) Assignees: Meiji Dairies Corporation, Tokyo (JP); Kyowa Hakko Bio Co. Ltd., Tokyo (JP)

( * ) Notice: Subject to any disclaimer, the term of this patent is extended or adjusted under 35 U.S.C. 154(b) by 0 days.

(21) Appl. No.: 10/537,401

(22) PCT Filed: Dec. 2, 2003

(86) PCT No.: PCT/JP03/15429
§ 371 (c)(1),
(2), (4) Date: Nov. 21, 2005

(87) PCT Pub. No.: WO2004/049830
PCT Pub. Date: Jun. 17, 2004

(65) Prior Publication Data
US 2006/0127492 A1    Jun. 15, 2006

(30) Foreign Application Priority Data
Dec. 2, 2002 (JP) .................................. 2002-350200

(51) Int. Cl.
*A61K 31/195* (2006.01)
*A61K 47/00* (2006.01)
*A61K 47/06* (2006.01)

(52) U.S. Cl. .................... 424/439; 514/561; 514/776

(58) Field of Classification Search .................. 514/561; 424/439, 450
See application file for complete search history.

(56) References Cited

U.S. PATENT DOCUMENTS

| | | |
|---|---|---|
| 4,687,782 A | 8/1987 | Brantman |
| 5,641,531 A | 6/1997 | Liebrecht et al. |
| 7,288,570 B2 * | 10/2007 | Verlaan et al. ............... 514/561 |

FOREIGN PATENT DOCUMENTS

| | | |
|---|---|---|
| CA | 2641667 A1 | 5/2000 |
| CN | 1366825 A | 9/2002 |
| DE | 298 08 637 U1 | 7/1998 |
| EP | 0 747 395 A1 | 12/1996 |
| FR | 2 758 243 A | 7/1998 |
| GB | 2 335 134 A | 9/1999 |
| JP | 8140628 A | 6/1996 |
| JP | 8198748 A | 8/1996 |
| WO | WO 99/49741 A | 10/1999 |
| WO | WO 00/64283 A | 11/2000 |

OTHER PUBLICATIONS

Health Publications article Oct. 2002: 3 pages.*
Soop, M., et al. 1988 J Appl Physiol 64(6): 2394-2399.*
Chinese Office Action dated Jun. 16, 2006.
Carlon M. Colker et al., "Effects of Supplemental Protein on Body Composition and Muscular Strength in Healthy Athletic Male Adults", Current Therapeutic Research, 2000, pp. 19-28, vol. 61, No. 1.
Database WPI Section CH, Week 199632 Derwent Publications Ltd., London, GB; AN 1996-316268 XP002271047.
Database WIP Section CH, Week 199641 Derwent Publications Ltd., London, GB; AN 1996-408309 XP002271048.
Patent Abstracts of Japan, vol. 010, No. 036 (C-328), Feb. 13, 1986.
International Search Report, 2004.
Canadian Office Action dated Aug. 6, 2010 issued in counterpart application No. 2,507,835.

* cited by examiner

*Primary Examiner* — Suzanne M Noakes
*Assistant Examiner* — Marsha M Tsay
(74) *Attorney, Agent, or Firm* — Sughrue Mion, PLLC

(57) ABSTRACT

A long-acting improver of muscular fatigue characterized by comprising 4 kinds of amino acids made up of leucine, isoleucine, valine and glutamine, and a whey protein component (whey protein and/or decomposition product of whey protein). At least one of a whey protein isolate (WPI), a whey protein concentrate (WPC), β-lactoglobulin, and α-lactalbumin is used as the whey protein. Novel food or drink, and pharmaceuticals which exhibit sustained recovery effects on muscular fatigue are provided.

6 Claims, No Drawings

SUSTAINED IMPROVER OF MUSCULAR FATIGUE

CROSS-REFERENCE TO RELATED PATENT APPLICATION

The present application is the U.S. national stage entry under 35 U.S.C. §371 of International Patent Application No. PCT/JP03/15429, filed Dec. 2, 2003, which claims priority from Japanese Patent Application No. 2002-350200, filed on Dec. 2, 2002.

TECHNICAL FIELD

The present invention relates to a sustained improver of muscular fatigue or food or drink for sustained improvement of muscular fatigue which comprises amino acids and a whey protein component.

BACKGROUND ART

Leucine, isoleucine and valine are called branched chain amino acids (BCAA) and a mixture of these three kinds of amino acids is known to have muscular fatigue recovery effect (e.g., see JP-A-8-198748). The mixture of the three kinds of BCAA has been widely used as nutrients by being made into granules or drinks, but immediately after being absorbed to the small intestine, it is relatively rapidly metabolized, and thus sustained effect on muscular fatigue recovery is unlikely obtained.

Also, nutrients comprising a whey protein or a decomposition product of whey protein or soy protein have been known, but no sustained action on muscular fatigue recovery has been known (e.g., see *Gastroenterology*, 7, 151-161 (1976) and *Gut*, 14, 494-501 (1974)).

On the other hand, as a mixed composition of the mixture of the three kinds of amino acids with a protein, a composition obtained by adding to an amino acid mixture of leucine, isoleucine and valine 2- to 30-fold amounts of a protein, followed by solidification, is also known (e.g., see JP-A-60-186261), but the protein is used only as an excipient and is not used for facilitating fatigue recovery effects.

DISCLOSURE OF THE INVENTION

It has been accepted that a nutrient comprising the BCAA mixture used for sports is taken once a day in the form of jelly or granules of about 2 to 3 g. Such administration is highly effective immediately after the administration, but it does not show sustained effect, because the amino acids in blood are metabolized and excreted gradually. Therefore, nutrient compositions having sustained effect on muscular fatigue recovery suitable for the administration method with once a day have been desired. Of course, it is the same in intended uses, for example for health care, health maintenance, and recovery of fatigue in daily life in addition to sports.

The present invention has been performed for the purpose of responding to the above requests in the art, the present inventors have studied widely from various aspects, taken note of necessity to formulate the other components to BCAA for the first time, and not only taken note of amino acids in numerous various components but also found necessity to formulate different components from the amino acids. And, the present inventors have taken note of glutamine in numerous amino acids and for the first time have taken note of whey protein components as the other components.

Thus, the present inventors have formulated glutamine and whey protein components in the BCAA mixture for a formulated composition of the BCAA mixture, then as a result of intensive study of the composition, have discovered that recovery effect of muscular fatigue is sustained, and have completed the present invention.

The present invention relates to the following (1) to (16).

(1) A sustained improver of muscular fatigue, which consists of leucine, isoleucine, valine, glutamine and a whey protein component.

(2) A sustained improver of muscular fatigue, which comprises, as active ingredients, leucine, isoleucine, valine, glutamine and a whey protein component.

(3) The improver according to (1) or (2), wherein the whey protein component is whey protein and/or a decomposition product of whey protein.

(4) The improver according to (3), wherein the whey protein is at least one selected from the group consisting of a whey protein isolate, a whey protein concentrate, $\beta$-lactoglobulin, and $\alpha$-lactalbumin.

(5) The improver according to any one of (1) to (4), which comprises leucine in an amount of 10 to 30 parts by weight, isoleucine in an amount of 5 to 15 parts by weight, valine in an amount of 5 to 15 parts by weight, glutamine in an amount of 5 to 15 parts by weight, and the whey protein component in an amount of 75 to 25 weight.

(6) The improver according to any one of (1) to (5), which comprises leucine in an amount of 20 parts by weight, isoleucine in an amount of 10 parts by weight, valine in an amount of 10 parts by weight, glutamine in an amount of 10 parts by weight, and the whey protein component in an amount of 50 parts by weight.

(7) The improver according to (6), wherein the whey protein component is a decomposition product of whey protein.

(8) A food or drink for sustained improvement of muscular fatigue, which comprises, as an active ingredients, leucine, isoleucine, valine, glutamine and a whey protein component.

(9) The food or drink according to (8), wherein the whey protein component is whey protein and/or a decomposition product of whey protein.

(10) The food or drink according to (9), wherein the whey protein is at least one selected from the group consisting of a whey protein isolate, a whey protein concentrate, $\beta$-lactoglobulin, and $\alpha$-lactalbumin.

(11) The food or drink according to any one of (8) to (10), which comprises leucine in an amount of 10 to 30 parts by weight, isoleucine in an amount of 5 to 15 parts by weight, valine in an amount of 5 to 15 parts by weight, glutamine in an amount of 5 to 15 parts by weight, and the whey protein component in an amount of 75 to 25 parts by weight.

(12) The food or drink according to any one of (8) to (11), which comprises leucine in an amount of 20 parts by weight, isoleucine in an amount of 10 parts by weight, valine in an amount of 10 parts by weight, glutamine in an amount of 10 parts by weight, and the whey protein component in an amount of 50 parts by weight.

(13) The food or drink according to (12), wherein the whey protein component is a decomposition product of whey protein.

(14) The use of leucine, isoleucine, valine, glutamine and a whey protein component for the manufacture of a sustained improver of muscular fatigue.

(15) The use of leucine, isoleucine, valine, glutamine and a whey protein component for the manufacture of food or drink for sustained improvement of muscular fatigue.

(16) A method of improving muscular fatigue sustainably, which comprises administering leucine, isoleucine, valine, glutamine and a whey protein component.

The present invention relates to a sustained improver of muscular fatigue which comprises leucine, isoleucine, valine, glutamine and a whey protein component. Since the present invention can be utilized as any of pharmaceuticals, foods and drinks, the present invention can provide sustained improvers of muscular fatigue or foods or drinks for the sustained improvement of muscular fatigue.

The present invention relates to the sustained improver of muscular fatigue or the food or drink comprising the above 4 kinds of the amino acids and the whey protein component, but includes any of the improvers or foods or drinks comprising them as active ingredients and the agents consisting of them.

In the sustained improvers of muscular fatigue or foods or drinks comprising 4 kinds of the amino acids and the whey protein component as active ingredients, generally, 4 kinds of the amino acids should be present independently as respective amino acid compounds, and the other amino acids, components of sustained improvers of muscular fatigue, foods or drinks, peptides and the like can be combined. Also, when a content of each amino acid of 4 kinds of the amino acids is known, mixtures or ingredients (e.g., peptides, decomposition products of peptides, foods, etc.) thereof which are not pure amino acids can be used. Furthermore, it is possible to combine the pure amino acids and the mixtures thereof at the desired ratio. Also, as for the whey protein components, it is similarly possible to use pure components or the ingredients (mixtures) thereof.

In the sustained improvers of muscular fatigue consisting of 4 kinds of the amino acids and the whey protein component, as 4 kinds of the amino acids, only 4 kinds of pure amino acid compounds are used, and the other amino acids, peptides, decomposition products of peptides, foods or drinks and the other components of sustained improvers of muscular fatigue are not combined. It is also the same for the whey protein components.

That is, the present invention includes both the improvers which consist of 4 kinds of the pure amino acids and the whey protein component and does not comprise the other components of sustained improvers of muscular fatigue, and the improvers or foods or drinks which contain them as active ingredients. Of course, in the former case, it is not prevented to use aids needed to preparations and water for making drinks, which are not the components of sustained improvers of muscular fatigue.

In the present invention, the whey protein and/or the decomposition product of whey protein is used as the whey protein component. The whey protein includes a whey protein isolate (WPI), a whey protein concentrate (WPC), an α-lactalbumin concentrate and a β-lactoglobulin concentrate, and the decomposition product of whey protein includes hydrolysate thereof. They are used alone or in combination of two or more.

WPCs are those where the whey produced at the production of cheese and casein is treated by methods such as ultrafiltration, gel filtration and lactose crystal separation to raise a protein content therein generally up to from 35 to 85% (as solid content).

WPI is different from WPC, and its protein content is raised up to about 95% (as solid content) by the method such as an ion exchange method.

The α-lactalbumin concentrate and the β-lactoglobulin concentrate can be obtained from WPI and WPC by fractionating and concentrating by the methods known in the art described in JP-B-3-60468.

The hydrolysate may be any peptides as long as they are obtained by the methods in the art, e.g., the method for obtaining by hydrolyzing with a protease derived from *Bacillus*, a protease derived from Actinomycetes, trypsin, chymotrypsin and the like as described in JP-A-6-343422, and are generally used for foods or drinks.

Also, the whey protein component may be not only the whey protein alone or the decomposition product of whey protein alone but also a mixture of both, and the decomposition product of whey protein is preferably used as the component.

A composition ratio of leucine, isoleucine, valine, glutamine and the whey protein component of the present invention includes leucine at 10 to 30 parts by weight, isoleucine at 5 to 15 parts by weight, valine at 5 to 15 parts by weight, glutamine at 5 to 15 parts by weight and the whey protein component at 75 to 25 parts by weight, preferably leucine at 16 to 24 parts by weight, isoleucine at 8 to 12 parts by weight, valine at 8 to 12 parts by weight, glutamine at 8 to 12 parts by weight and the whey protein component at 60 to 40 parts by weight, and most preferably leucine at 20 parts by weight, isoleucine at 10 parts by weight, valine at 10 parts by weight, glutamine at 10 parts by weight and the whey protein component (e.g., decomposition product of whey protein) at 50 parts by weight. Also, the composition ratio of leucine, isoleucine, valine and glutamine with the whey protein component includes leucine, isoleucine, valine and glutamine at 25 to 75 parts by weight and the whey protein component at 75 to 25 parts by weight, preferably leucine, isoleucine, valine and glutamine at 40 to 60 parts by weight and the 60 to 40 parts by weight of the whey protein component, and most preferably leucine, isoleucine, valine and glutamine at 50 parts by weight and the whey protein component at 50 parts by weight.

Besides, the parts by weight of the whey protein component are referred to net weight of whey protein or decomposition product of whey protein contained in the whey protein component such as WPI and WPC (the same hereinafter).

In the present invention, the sustained improver of muscular fatigue or the food or drink for the sustained improvement of muscular fatigue may be any of those as long as they are pharmaceuticals or foods or drinks which can be used for the prevention or the treatment of muscular fatigue.

Kinds of foods or drinks can exemplify nutrient compositions such as tablets, capsules and liquid formations sold as healthy foods (including foods for specified health use, nutrient functional foods, foods or drinks for sports, and the like), juices, soft drinks, teas, lactic acid bacteria beverages, fermented milk, milk products (processed milk, skim milk and the like), snacks (candy, drops, chocolate, jelly, biscuit, cookie, ice cream, etc.). In the case of anticipating the recovery effect of muscular fatigue, it is preferred that it is orally used as the healthy food comprising effective amounts of leucine, isoleucine, valine and glutamine and a whey protein component. In the case of using as the pharmaceutical, for example, also preferred are oral agents such as tablets, capsules, syrup, and sublingual tablets.

Therefore, the foods or drinks for the sustained improvement of muscular fatigue include all the above foods or drinks. Also, the improver of the present invention include all of those formulated in the above usual foods or drinks in addition to those formulated into tablets, capsules, liquid formulation and the like and those formulated into dosage forms similar to pharmaceuticals such as supplements and drinks. The pharmaceuticals include all of those formulated into the pharmaceuticals according to the standard methods.

Generally known methods are applied for the formulation of the dosage forms orally administered as the healthy food or the pharmaceutical, and for example, various excipients, lubricants, binders, disintegrants, suspending agents, isotonic agents, emulsifiers and the like may be contained.

Carriers used for the formulation include, for example, water, injectable distilled water, saline, glucose, sucrose, mannite, lactose, mannitol, sorbitol, lactitol, xylitol, erythritol, starch, cellulose, methylcellulose, carboxymethylcellulose, hydroxypropylcellulose, alginic acid, talc, citric acid, calcium carbonate, calcium hydrogen phosphate, magnesium stearate, urea, silicone-resin, sorbitan fatty acid ester, glycerate ester and the like.

Leucine, isoleucine, valine, glutamine and the whey protein component in the present invention can be contained at 1 to 1000 mg, preferably from 10 to 900 mg, and most preferably from 100 to 800 mg, per g of the preparation or the food or drink.

Ingestion amount and frequency are different depending on administration route, form, age, body weight, condition and the like, but as 4 kinds of the amino acids and the whey protein component, generally the oral amount is from 0.5 to 4 g, preferably from 1 to 3 g and most preferably from 2 to 3 g. For example, for the tablet containing 500 mg of leucine, isoleucine, valine, glutamine and the whey protein component, it is preferable to ingest 2 to 3 tablets twice a day. Besides, 4 kinds of the amino acids and the decomposition product of whey protein (AAs+P described below) were orally administered at 0.5 g per 100 g of body weight (10-weeks old SD male rats) once a day, and after a month, no death case was observed.

The preparation method when the present invention is used for foods or drinks other than the healthy foods is the same as that of usual foods or drinks except that leucine, isoleucine, valine, glutamine and the whey protein component are added. For example, the drinks can be prepared by dissolving leucine, isoleucine, valine, glutamine and the whey protein component and various additives in an appropriate amount of water, if necessary. Also, as the foods, for example, snacks such as candy, drops, chocolate, Jelly, biscuit and cookie can be prepared by adding leucine, isoleucine, valine, glutamine and the whey protein component, using necessary additives and further appropriate carrier, e.g., wheat, rice powder, starch, corn starch, soy beans and the like and forming into appropriate forms according to the standard methods.

Hereinafter, the present invention is specifically explained below based on Test Example showing the prevention or improvement effects of muscular fatigue of the composition (hereinafter, may also be referred to as KAAM) in which leucine, isoleucine, valine, glutamine and the whey protein component are added, and Examples showing formulation examples of the preventive or therapeutic pharmaceuticals as sustained improvers of muscular fatigue, foods or drinks of the present invention, but the invention is not limited to these specific examples.

BEST MODE FOR CARRYING OUT THE INVENTION

Test Example 1

Effects of KAAM on Muscular Proteolysis After Exercise:

Three-weeks old SD male rats were used by dividing into the following 3 groups (n=15). Distilled water was orally administered at 30 ml per kg of body weight to the rats in Vehicle group. A mixture solution of leucine, isoleucine, valine, and glutamine (weight ratio of 2:1:1:1) was prepared (a mixture concentration is 1 g per 30 ml of distilled water), and it was orally administered at 30 ml per kg of body weight to the rats in AAs group (an administered amount as the mixture is 1 g per kg of body weight). A mixture solution of leucine, isoleucine, valine, glutamine and the whey protein component (weight ratio of 2:1:1:1:5) was prepared (a mixture concentration is 1 g per 30 ml of distilled water), and it was orally administered at 30 ml per kg of body weight to the rats in AAs+P group (an administered amount as the mixture is 1 g per kg of body weight).

As the decomposition product of whey protein, one produced by the following method was used.

WPI (protein content 92%) (1,000 g) was dissolved in 8,800 g of water. Bioprase (manufactured by Nagase Biochemical Ltd.) (2,200 units per g of protein), 1,300 unites per g of protein of trypsin (manufactured by Novo), 90 units per g of protein of chymotrypsin (manufactured by Novo) and 1,100 units per g of protein of actinase (manufactured by Kaken Pharmaceutical Co., Ltd.) were added, and hydrolyzed at 50° C. for 20 hours while adjusting pH at 7.5 with 10% sodium hydroxide solution. The resulting mixture was ultrafiltered by an ultrafiltration filter with a fractionation molecular weight of 20,000 to eliminate the enzymes and insoluble hydrolysate. Further, the solution was desalted until an electric conductivity became $1/10$ using an electrodialyzer and then dried to yield the decomposition product of whey protein (content of decomposition product of protein: 94%).

The rats in 3 groups were raised precedently for 3 days, and then an exercise (slope 6 degree, speed 7 to 25 m/min, 30 min) was given once a day for 3 days to familiarize a treadmill. After 18 hours of fasting and 1 hour of cessation of water drinking, the treadmill exercise (slope 6 degree, speed 15 to 30 m/min, 30 min) was given for one hour. Immediately after the exercise, the above distilled water, the amino acid mixture solution or the amino acid and decomposition product of whey protein mixture solution (30 ml per kg of body weight, as the administered amount of mixture, 1 g/kg of body weight) was orally administered to each group, 5 rats in each group was anatomized 6 hours after the administration, musculus soleus was removed from both legs, and it was incubated in Krebs-Henseleit bicarbonate buffer under a gas flow of 95% $CO_2$-5% $O_2$ for 2 and a half hours. Tyr (tyrosine) release rate can be used as an index of a degradation rate of musculus soleus cytoplasmic protein. Thus, concentration of Tyr in the buffer was measured to determine Try release rate. On the other hand, apart from the above 3 groups, according to the similar method as that of the above 3 groups except that the exercise and administration were not carried out, Tyr release rate at 0 hour was measured. The Try release rate at 0 hour was used as the Try release rate in a non-exercise group.

The Tyr release rates in the non-exercise group, Vehicle group, AAs group and AAs+P group are shown in Table 1.

TABLE 1

|  | Hours after administration | Tyr (nmol/g tissue/2 h) | p-Value for Vehicle |
|---|---|---|---|
| non-exercise group | No administration | 346 ± 65 | — |
| Vehicle group | After 6 hours | 399 ± 63 | — |
| AAs group | After 6 hours | 358 ± 83 | 0.3998 |
| AAs + P group | After 6 hours | 293 ± 71* | 0.0359 |

*There is a significant difference between Vehicle group (p < 0.05).

As a result, as shown in Table 1, the Tyr release rate from musculus soleus which is an index of the decomposition rate of musculus cytoplasmic serous protein was significantly reduced in AAs+P group compared to Vehicle group (Student's t-test, p-value <0.05), but there was no significant difference between AAs group and Vehicle group.

Also, the Tyr release rate in AAs group is nearly the same levels as those in the non-exercise group whereas the Tyr release rate in AAs+P group was kept lower than that in the non-exercise group and the suppressing effect on releasing Tyr was obviously sustained in AAs+P group.

Besides, the Tyr amount was measured by Waalkes et al's fluorescent method using 1-nitroso-2-naphthol [T. P. Waalkes, S. Udenfriend, *J Lab. Clin. Med.*, 50, 733 (1957)].

As the above, it has been confirmed that muscular proteolysis after the exercise is persistently suppressed in the present invention where the decomposition product of whey protein was added. Besides, the same effect was confirmed in the case using WPI in place of the decomposition product of whey protein.

Example 1

Erythritol (1,375 g) and 50 g of sucrose fatty acid ester, 350 g of citric acid and 125 g of flavoring agent were added to and mixed with a granulated amino acid nutrient component mixture made up of 600 g of leucine, 300 g of isoleucine, 300 g of valine, 300 g of glutamine and 1,500 g of the decomposition product of whey protein used in Test Example 1.

Next, tablets containing 500 mg of KAAM per tablet (hereinafter referred to as tablet 1) were manufactured using a rotary type tabletting machine (trade name: AP-15 type, manufactured by Hatake Ironworks) loading a plane mallet with a diameter of 13 mm.

Example 2

One where a granulated amino acid nutrient component mixture made up of 600 g of leucine, 300 g of isoleucine, 300 g of valine, 300 g of glutamine and 1,200 g of the decomposition product of whey protein used in Test Example 1, and 1,375 g of erythritol were formulated was placed in a fluidized bed granulating dryer (manufactured by Glat, WSG-5 type), a binder solution where 100 g of maltose was dissolved in 1,500 g of purified water was sprayed to yield granulation. Sucrose fatty acid ester (40 g) was added to 3,660 g of the resultant granulated dried matter to make granules for tabletting.

Next, the granules were compressed and molded using the rotary type tabletting machine (trade name: AP-15 type, manufactured by Hatake Ironworks) loading a plane mallet with a diameter of 15 mm to manufacture the tablets containing 450 mg of KAAM per tablet (hereinafter referred to as tablet 2). As with the above, the tablets (hereinafter referred to as tablets 3, 4, and 5) were manufactured using hydrolysates of WPC, β-lactoglobulin and α-lactalbumin, respectively.

Example 3

Water (20 g) was added to 2.0 g of leucine, 1.0 g of isoleucine, 1.0 g of valine, 1.0 g of glutamine, 4.0 g of the decomposition product of whey protein used in Test Example 1, 13.5 g of soy bean protein, 2.5 g of chitosan, 1.5 g of arginine, 0.05 g of caffeine, 85.0 g of wheat, 50.0 g of shortening, 55.0 g of granulated sugar, and 1.5 g of baking powder, the mixture was kneaded to prepare dough and molded and then cookies were baked by the standard method.

While the present invention has been described in detail and with reference to specific embodiments thereof, it will be apparent to one of skill in the art that various changes and modifications can be made therein without departing from the spirit and scope thereof. All references cited herein are incorporated in their entirety.

This application is based on Japanese application No. 2002-350200 filed on Dec. 2, 2002, the entire contents of which are incorporated hereinto by reference.

INDUSTRIAL APPLICABILITY

The present invention provides amino acid nutrient compositions which exhibit sustained recovery effects on muscular fatigue.

The invention claimed is:

1. A composition for a sustained treatment of muscular fatigue, which consists of leucine, isoleucine, valine, glutamine and a whey protein component, wherein the whey protein component is at least one selected from the group consisting of a whey protein isolate, a whey protein concentrate, β-lactoglobulin, α-lactalbumin, and a whey protein hydrolysate.

2. The composition according to claim 1, wherein the amount of leucine is 10 to 30 parts by weight, the amount of isoleucine is 5 to 15 parts by weight, the amount of valine is 5 to 15 parts by weight, the amount of glutamine is 5 to 15 parts by weight, and the amount of the whey protein component is 75 to 25 parts by weight, each based on the total weight of the composition.

3. The composition according to claim 1, wherein the amount of leucine is 20 parts by weight, the amount of isoleucine is 10 parts by weight, the amount of valine 10 parts by weight, the amount of glutamine is 10 parts by weight, and the amount of the whey protein component is 50 parts by weight, each based on the total weight of the composition.

4. A method of sustainably treating muscular fatigue, which comprises administering a composition consisting of leucine, isoleucine, valine, glutamine and a whey protein component to a subject in need of sustained treatment of muscular fatigue, wherein the whey protein component is at least one selected from the group consisting of a whey protein isolate, a whey protein concentrate, β-lactoglobulin, α-lactalbumin, and a whey protein hydrolysate.

5. The method according to claim 4, wherein the composition consists of leucine in an amount of 10 to 30 parts by weight, isoleucine in an amount of 5 to 15 parts by weight, valine in an amount of 5 to 15 parts by weight, glutamine in an amount of 5 to 15 parts by weight, and the whey protein component in an amount of 75 to 25 parts by weight based on the total weight of the composition.

6. The method according to claim 4, wherein the composition consists of leucine in an amount of 20 parts by weight, isoleucine in an amount of 10 parts by weight, valine in an amount of 10 parts by weight, glutamine in an amount of 10 parts by weight, and the whey protein component in an amount of 50 parts by weight based on the total weight of the composition.

* * * * *